(12) United States Patent
White

(10) Patent No.: US 6,703,012 B1
(45) Date of Patent: Mar. 9, 2004

(54) COMPOSITIONS CONTAINING FRAGRANCES AND POWDERED WATER-SOLUBLE POLYMERS AND TOILET BLOCKS PRODUCED THEREFROM

(75) Inventor: Michael John Robert White, Amsterdam (NL)

(73) Assignee: International Flavors & Fragrances Inc., New York, NY (US)

( * ) Notice: Subject to any disclaimer, the term of this patent is extended or adjusted under 35 U.S.C. 154(b) by 401 days.

(21) Appl. No.: 09/336,051

(22) Filed: Jun. 18, 1999

(30) Foreign Application Priority Data

Apr. 27, 1999 (EP) ............................................. 99303179

(51) Int. Cl.⁷ ............................. A61L 11/00; A61L 9/00; A61K 9/14

(52) U.S. Cl. ..................... 424/76.7; 424/76.1; 424/489; 523/102

(58) Field of Search ................................ 424/76.7, 489, 424/76.1; 523/102

(56) References Cited

U.S. PATENT DOCUMENTS

| | | | |
|---|---|---|---|
| 4,339,356 A | 7/1982 | Whyte | |
| 5,543,439 A | 8/1996 | McDermott et al. | |
| 5,578,559 A | 11/1996 | Dolan et al. | 512/192 |
| 6,103,681 A | 8/2000 | Chantler et al. | 510/191 |

FOREIGN PATENT DOCUMENTS

| | | |
|---|---|---|
| EP | 0 728 804 A | 8/1996 |
| EP | 95308399.5 | 10/1998 |

*Primary Examiner*—Thurman K. Page
*Assistant Examiner*—Amy E Pulliam
(74) *Attorney, Agent, or Firm*—Joseph F. Leightner

(57) ABSTRACT

Described is a composition of matter comprising a powdered, water-soluble, water-dispersible or water-swellable polymer, a compatible fragrance, either as a blend of fragrance with polymer or separately mixed, and one or more surfactants. The polymer may be extruded polyvinyl alcohol or partially hydrolyzed polyvinyl acetate. Also described is a toilet element moulded from the composition of matter, which may be either a toilet rim block for use in a toilet bowl, or a free-standing block for use in a toilet cistern, and processes for comparing the composition of matter and toilet element.

4 Claims, 3 Drawing Sheets

Figure 1:
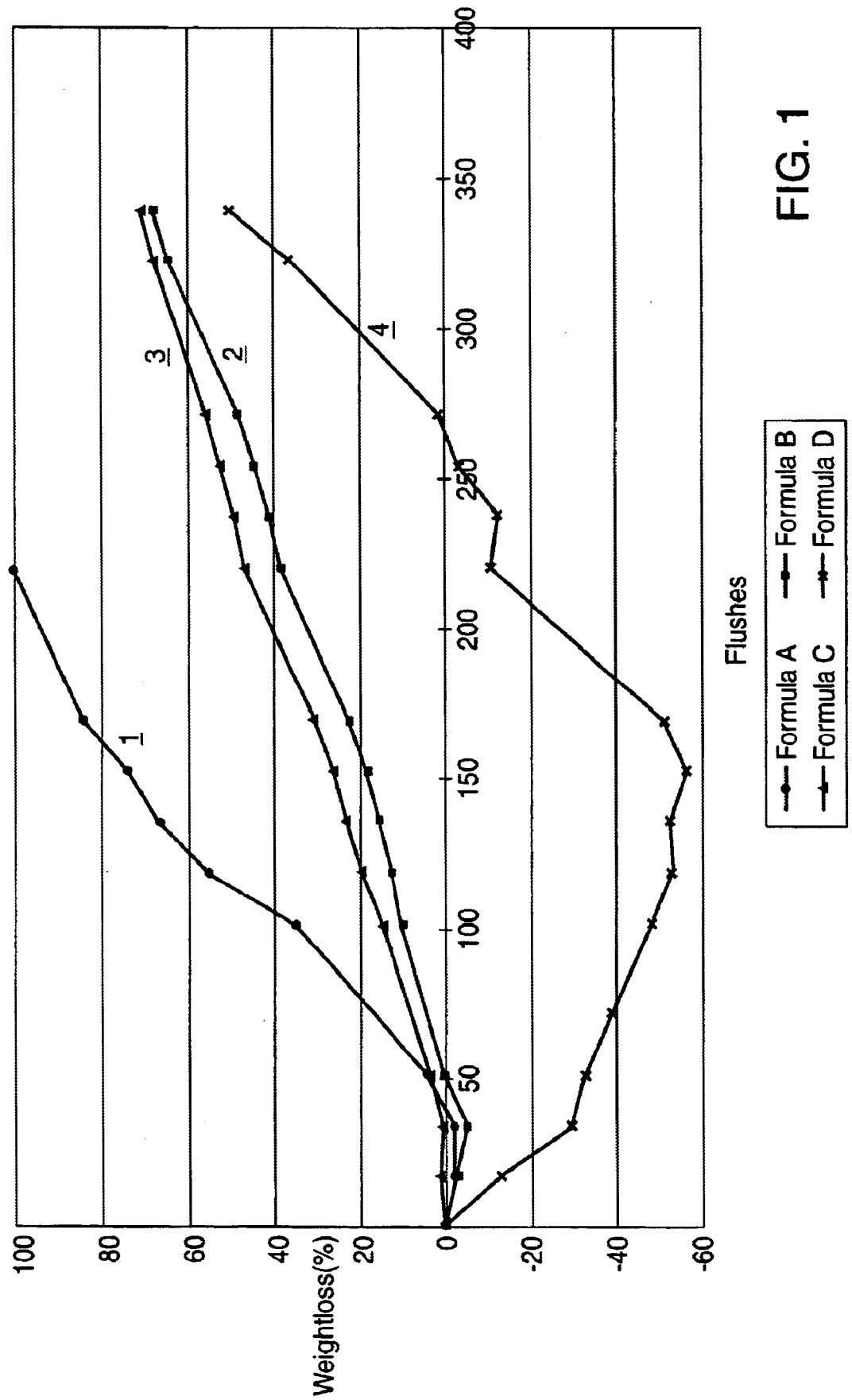

The present invention relates to powdered water-soluble polymers and, more particularly, to the use of powdered water-soluble polymers in toilet block applications.

COMPOSITIONS CONTAINING FRAGRANCES AND POWDERED WATER-SOLUBLE POLYMERS AND TOILET BLOCKS PRODUCED THEREFROM

RELATED CO-PENDING PATENT APPLICATIONS

This application claims foreign priority benefits under Tide 35 U.S.C. §119 of European Patent Application No. 99/303179.8 filed on Apr. 27, 1999 (tile: "POWDERED WATER SOLUBLE POLYMERS").

BACKGROUND OF THE INVENTION

The present invention relates to powdered water-soluble polymers and, more particularly, to the use of powdered water-soluble polymers in toilet block applications.

U.S. Pat. No. 5,543,439 (McDermott, et al) (the specification for which is incorporated by reference herein) discloses a water-soluble composition comprising extruded polyvinyl alcohol or partially hydrolyzed polyvinyl acetate having admixed therewith a compatible fragrance and one or more other components, particularly suitable for use in the fabrication of toilet rim blocks. Polyvinyl alcohol and partially hydrolyzed polyvinyl acetate are water-soluble, biodegradable resins having advantageous aroma control release properties and solubility/dispersibility characteristics desirable for toilet rim blocks. In U.S. Pat. No. 5,543,439, the extrusion and subsequent comminution of the polyvinyl alcohol or partially hydrolyzed polyvinyl acetate provides facile control of the size of the dispersed entities and the overall size of the particulate fragrancing polymers, which, in turn, provides control over the ultimate advantageous properties of the particulate fragranced polymers described therein. Until U.S. Pat. No. 5,543,439, the advantages of polyvinyl alcohol and partially hydrolyzed polyvinyl acetate had not previously been obtained in toilet block applications, and other additives had to be included in the toilet block compositions in order to provide the desired aroma control release and solubility/dispersibility characteristics.

Although the water-soluble compositions of U.S. Pat. No. 5,543,439 have excellent aroma and solubility properties, however, the foaming performance of these compositions is less than optimal.

It is, therefore, an object of the present invention to provide a water-soluble, water-swellable or water-dispersible composition having improved foaming performance, without compromising excellent aroma behavior, life-time performance and solubility/dispersibility characteristics desirable for toilet block applications.

SUMMARY OF THE INVENTION

According to the present invention, there is provided a composition of matter which comprises a powdered, water-soluble, water-swellable or water-dispersible polymer, a compatible fragrance, either as a blend of fragrance with polymer or separately mixed, and one or more surfactants.

The composition of matter of the present invention, has, unexpectedly and advantageously, excellent foaming properties, better than the compositions of U.S. Pat. No. 5,543,439 (the specification for which is incorporated by reference herein) and conventional toilet elements, as well as excellent aroma behavior, life-time performance and solubility/dispersibility characteristics, which are comparable, and at least as good as, the aroma properties, life-time performance and solubility/dispersibility characteristics of a the compositions of U.S. Pat. No. 5,543,439.

Preferably, the composition of matter comprises 20% polymer and 5% fragrance, separately mixed, or 25% of an 80:20 polymer:fragrance blend.

Preferably, (a) the polymer is extruded polyvinyl alcohol or partially hydrolyzed polyvinyl acetate (50–90% partially hydrolyzed), (b) the one or more surfactants comprises a combination of sodium dodecylbenzenesulfonate and sodium toluenesulfonate in a weight ratio of from 1:5, to 5:1 (hereinafter referred to as 'LABS'); and (c) the fragrance comprises one or more polar primary alcohols, e.g., n-octyl alcohol or n-nonyl alcohol.

The composition of the present invention may, further, optionally contain a filler such as sodium sulphate or any one of a disinfecting or sanitizing agent, a coloring agent, a bleaching agent, a lime-scale removing agent, a deodorizing agent, a stain-inhibiting agent, a water-softening agent, a rheological control agent, a preservative, an antioxidant, a stabilizer, a dispersant and/or a foam booster.

Also provided are a toilet element, which may be a toilet rim block for use in a toilet bowl, or a free-standing block for use in a toilet cistern, molded using the composition of the present invention and processes for preparing the composition of matter and toilet element of the present invention.

DETAILED DESCRIPTION OF THE INVENTION AND DRAWINGS

In order that the invention may be more readily understood, and so that further features thereof may be more readily appreciated, examples of the invention will now be described, by way of example only, with reference to the accompanying drawings, in which:

FIG. 1 is a graph showing weight loss (%) versus number of flushes for formulation A of Example 1 of the present application, identified by reference numeral 1, formulation B of Example 1 of the present application, identified by reference numeral 2, formulation C of Example 1 of the present application, identified by reference numeral 3, and formulation D of Example 1 of the present application, identified as reference numeral 4.

Figure 2:
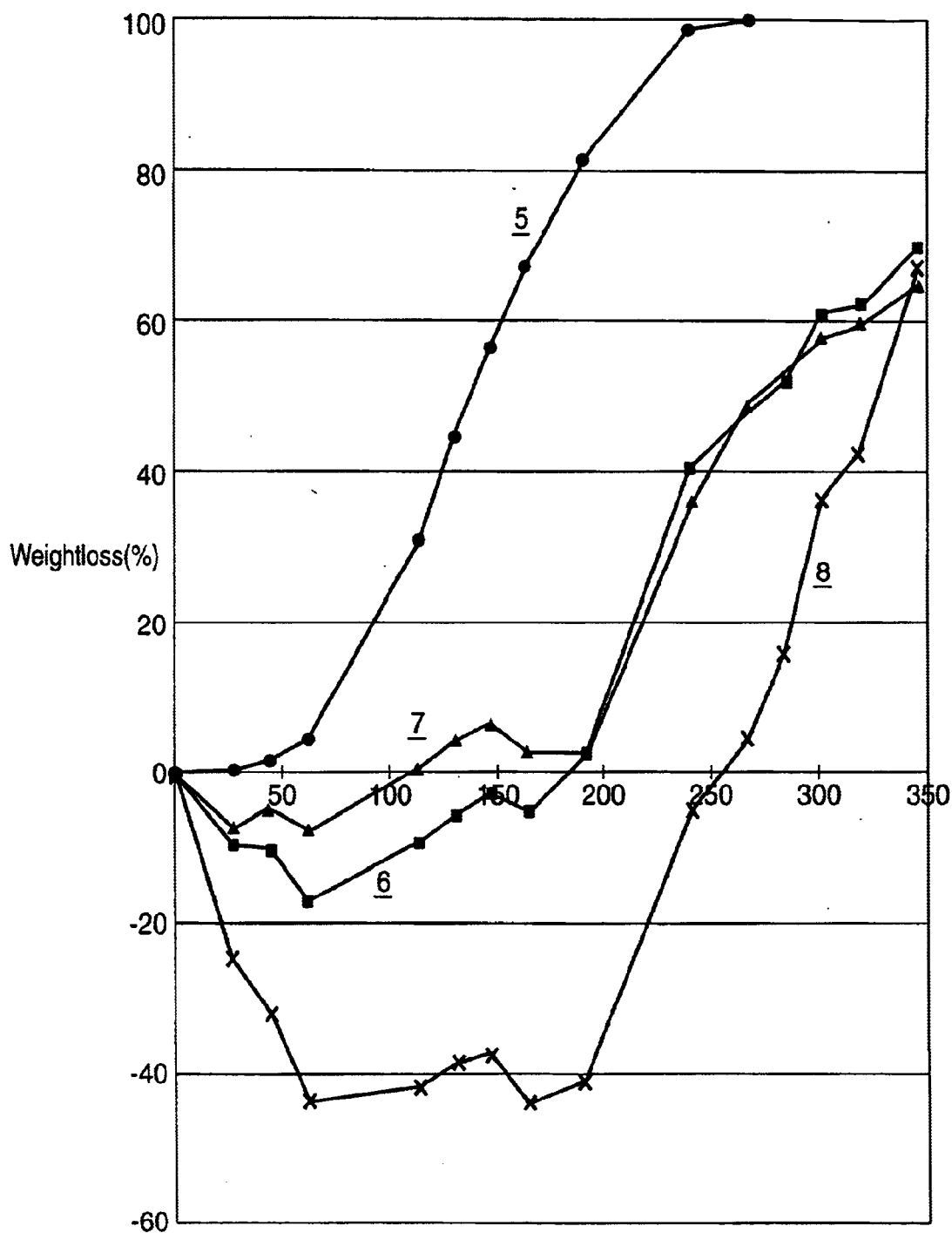
Figure 3:
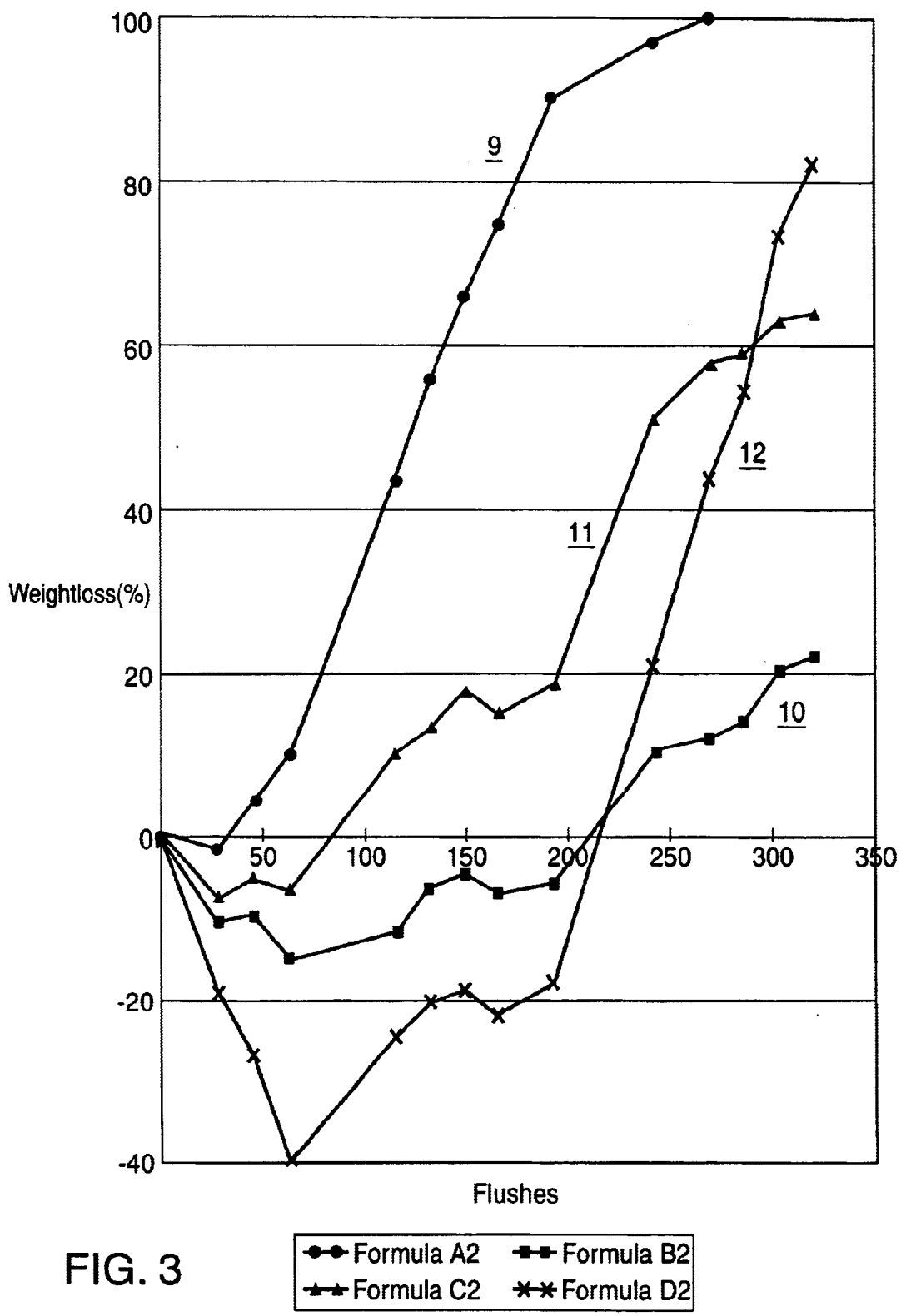

FIG. 2 is a graph showing weight loss (%) versus number of flushes for formulation A1 of Example 2 of the present application, identified as reference numeral 5, formulation B1 of Example 2 of the present application, identified as reference numeral 6, formulation C1 of Example 2 of the present application, identified as reference numeral 7, and formulation D1 of Example 2 of the present application, identified as reference numeral 8; and FIG. 3 is a graph showing weight loss (%) versus number of flushes for formulation A2 of Example 2 of the present application, identified as reference numeral 9 formulation B2 of Example 2 of the present application, identified as reference numeral 10 versus formulation C2 of Example 2 of the present application, identified as reference numeral 11, and formulation D2 of Example 3 of the present application, identified as reference numeral 12.

A composition of matter of the present invention comprises a powdered, water-soluble, water-swellable or water-dispersible polymer, a compatible fragrance and one or more surfactants.

The polymer acts as a binder/matrix for the various components of the composition and controls metering of the active ingredients when the final product comes into contact with water.

The solubility/dispersibility characteristics of the polymer are chosen to provide a desired degree and rate of solubility/dispersibility which, in the case of a toilet element, allows the toilet element to dissolve or disperse away over a desired period of time, preferably weeks, thereby allowing the contents of the toilet element to be released in a controlled manner. The polymer may be either water-soluble (i.e. capable of dissolving in water), water-dispersible (i.e. capable of dispersing in water without leaving any significant solid residue) or water-swellable (i.e. capable of disintegrating in water without leaving any significant solid residue).

An example of a polymer suitable for use in the composition of the present invention is extruded polyvinyl alcohol or partially hydrolyzed polyvinyl acetate, preferably having a number average molecular weight of between about 15,000 and 68,000.

The polyvinyl alcohol or partially hydrolyzed polyvinyl acetate may, for example, be prepared, first by polymerizing (via a "free radical" polymerization mechanism) vinyl acetate having the formula:

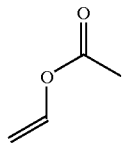

according to the reaction:

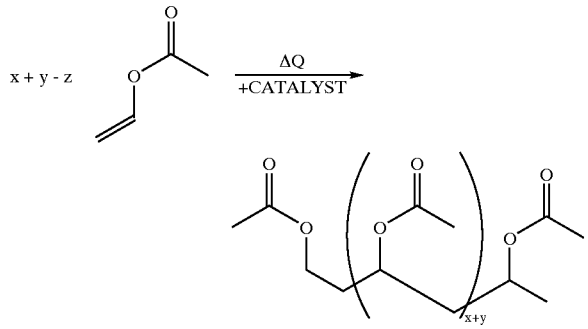

thereby forming a polyvinyl acetate, wherein x+y are such that the number average molecular weight of the final product is between 15,000 and 68,000. The resulting polyvinyl acetate may then be hydrolyzed, first to form a partially hydrolyzed polyvinyl acetate according to the reaction:

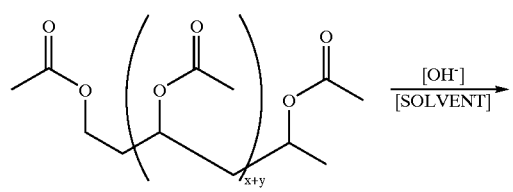

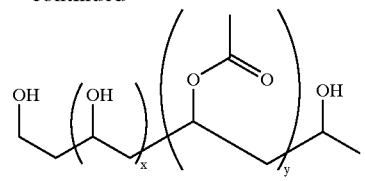

or a mixture of polyvinyl alcohol and partially hydrolyzed polyvinyl acetate according to the reaction:

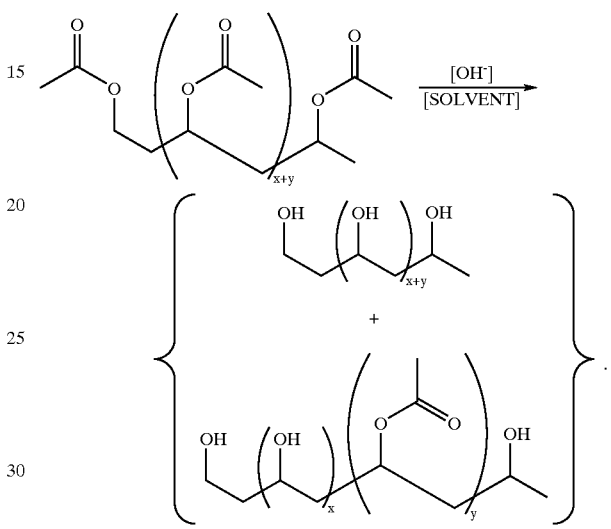

If desired, the partially hydrolyzed polyvinyl acetate may be further hydrolyzed to form polyvinyl alcohol without any acetyl groups present, according to the reaction:

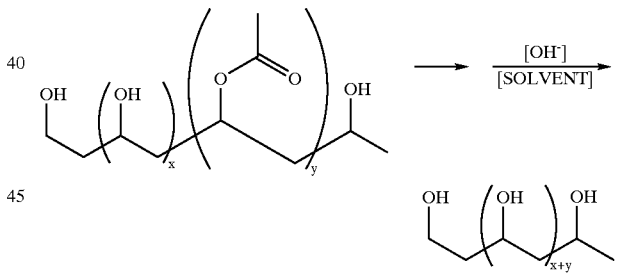

wherein x+y are such that the number average molecular weight of the final polymer is between about 15,000 and 68,000.

The maximum mole ratio of acetyl moiety:hydroxyl moiety in the partially hydrolyzed polyvinyl acetate is preferably about 1:3, such a polymer being water-soluble at ambient temperatures, e.g., 25° to 35° C.

The polymer used in the compositions of the present invention is in powdered form. The polymer is first extruded, using either a single screw or double screw extruder, and the extruded tow is then cooled (without being immersed in water) by any available suitable means, such as belts, blowers and the like. The cooled extrudate, which comprises a matrix with dispersed entities, is then ground to form a powder by means known in the art.

In particular, the polymer may be ground using the cryogenic grinding technique of U.S. Pat. No. 4,934,609 (Lindauer et al) (the specification for which is incorporated by reference herein). According to this technique, polymeric particles are produced by means of the process of first extruding a mixture of fragrance and polymer and quickly chilling the extrudate through a pelletizing operation and into an inert cooling liquid having a temperature in the range of from about 5° C. up to about 60° C.; then cryogenically grinding the resultant product using liquid nitrogen, liquid air or other cryogenic cooling agent at a pressure in the range of from about 1 atmosphere up to about 50 atmospheres, and to a particle size of, for example, from about 10 up to about 500 microns. For example, 25% hydrolized polyvinyl acetate may be extruded in a Hoake Plasticorder, with perfume. The resulting tow is quickly chilled in a liquid-quenching medium (water at 5° C.) and pelletized. The resulting pellets containing fragrance are then cryoground using liquid nitrogen to achieve an average particle size of 212 microns.

The nature of the cryogenic grinding apparatus useful in the practice of this invention is exemplified by several of those set forth in *Plastics Technology/Manufacturing Handbook and Buyers' Guide*, Volume 30, No. 7, mid-June 1984, pages 234, 240, 242 and 243, published by the Bill Publication Corporation of New York, N.Y. and are exemplified as follows:

1. The "CRYO-GRIND®" cryogenic grinding system manufactured by the Air Products and Chemicals Inc. of Allentown, Pa.
2. Cryogenic Pulverizers manufactured by Pallmann Pulverizers Co., Inc.
3. Wedco Cryogenic Pulverising System manufactured by Wedco, Inc.

In addition to the use of a single extruder, a series of extruders can also be used to form the extrudate.

The extrusion and subsequent comminution of the extrudate to form a powder enables the facile control of the size of the dispersed entities and the overall size of the particulate fragrancing polymers, which, in turn, provides control over the ultimate, advantageous and unexpected properties of the particulate fragranced polymers taught herein. The powdered polymer provides an improved barrier to fragrance diffusion, giving greater control over fragrance release, and therefore better fragrance performance as compared to the water-soluble compositions of U.S. Pat. No. 5,543,439 and the compositions of conventional toilet block elements.

The polymer may contain a plasticizer to enhance thermal stability and to allow the polymer to be extruded, and to maintain the shape and structural integrity of the final product during handling and contact with water. In the case of polyvinyl alcohol or partially hydrolyzed polyvinyl acetate, the amount of plasticizer contained in the polymer may vary from about 0 up to 13% by weight of the polyvinyl alcohol or partially hydrolyzed polyvinyl acetate. (Where a commercially available polyvinyl alcohol or partially hydrolyzed polyvinyl acetate is used, e.g. VINEX®, this presupposes that the commercially available polyvinyl alcohol or partially hydrolyzed polyvinyl acetate already contains approximately 2% by weight plasticizer.) Some polyvinyl alcohol materials, e.g. AIRVOL® 205, however, need not be plasticized to be used for the purposes of the invention. Thus, the total plasticizer range can vary from about 0% up to about 15%.

Examples of polar plasticizers suitable for use with polyvinyl alcohol or partially hydrolyzed polyvinyl acetate polymers include glycerine, triethanolamine, ethylene glycol, propylene glycol, diethylene glycol, dipropylene glycol, diethanolamine and methyldiethylamine.

Compatible fragrances suitable for use in the composition of the present invention include one or more highly polar primary organic alcohols, or mixtures thereof. For example, the following "compatible" rose fragrance formulation of GB-B-2,290,300 (International Flavors & Fragrances Inc.) may be used:

| Ingredient | Parts by Weight |
|---|---|
| geraniol ex palmarosa oil | 0.5 |
| nerol | 2.0 |
| L-citronellol | 3.1 |
| D-citronellol | 3.8 |
| β-phenyl ethyl alcohol | 2.0 |
| o-(2-hydroxyl-1-ethyl)-methylbenzene | 4.0 |
| 5-phenyl-3-methyl-1-pentanol | 5.6 |

The compositions of the present invention may contain, for example, from 1 up to about 20% by weight of a compatible fragrance and the fragrance may be included in the compositions of the present invention either as a polymer:fragrance blend, or separately mixed.

If the compatible fragrance is to be included in a composition of the present invention in the form of a polymer-:fragrance blend, the compatible fragrance may be introduced into the extruder at the time of extruding the polymer. In the case of polyvinyl alcohol or partially hydrolyzed polyvinyl acetate, where 5 to 10% by weight of the composition of compatible fragrance is added to the extruder, it is preferable to add hydrophobic silica to the compatible fragrance, prior to feeding into the extruder. For certain, but not all polyvinyl alcohols or partially hydrolyzed polyvinyl acetates, where from about 10% up to about 20% by weight of the composition of compatible fragrance is added to the extruder, it is necessary to add hydrophobic silica to the compatible fragrance prior to feeding into the extruder. The weight ratio of hydrophobic silica:compatible fragrance when the compatible fragrance is present in an amount of from about 10 up to about 20% is preferably from about 1:1 silica:compatible fragrance up to about 1:2 silica-compatible fragrance. An example of hydrophobic silica useful, in this respect, is SIPERNAT® D17 silica.

Alternatively, the compatible fragrance may be directly mixed with the powdered polymer, after the extrusion step, to form a composition of the present invention.

The compositions of the present invention also contain one or more surfactants. The following surfactants, which have both detergent and foaming properties, are useful in the compositions of the present invention:

MARLON® ARL supplied by Hüls America; Hüls AG (sodium dodecylbenzenesulfonate and sodium toluenesulfonate, a white to yellow powder, density 470 g/l, pH8, 80% active matter);

STANDAPOL® 7023 (an anhydrous blend of Cocamide DEA and DEA-Myreth Sulfate detergent);

WITCONATE® AOK manufactured by Witco Chemical Company (solid anionic α-sulfonate); and WITCONATE® 90 FLAKE manufactured by Witco Chemical Company (solid anionic α-sulfonate).

Additional examples of surfactants having both detergent and foaming properties are alkyl benzene sulfonates, such as n-octyl benzene sulfonate (sodium salt), and sodium lauryl sulfate.

The following surfactants are useful for their detergent properties, but cannot be depended upon for their foaming properties:

PLURONIC® F88 (a block copolymer of ethylene oxide and propylene oxide) manufactured by BASF;

PLURONIC® F77 (a block copolymer of ethylene oxide and propylene oxide) manufactured by BASF; and

WITCONATE® 90.

The compositions of the present invention are able to contain higher levels of surfactant as compared to the compositions of U.S. Pat. No. 5,543,439 and, thus, have improved foaming and cleaning properties.

In addition to the above-mentioned components, the compositions of the present invention may, optionally, contain other ingredients, for example, disinfecting or sanitizing agents, coloring agents, foam boosters, bleaching agents, preservatives, lime-scale removing agents, deodorizing agents, antioxidants, stabilizers, dispersants, stain-inhibiting agents, water-softening agents and/or Theological control agents. These may, for example, be added to the extruder containing the polymer during extrusion of the polymer, or may be separately mixed with the powdered polymer after the extrusion step.

Suitable color additives include, for example, Acid Blue No. 19 manufactured by Sandoz Pharmaceutical Corporation of Hanover, N.J.

Examples of foam boosters suitable for use in the compositions of the present invention include:

INCROMIDE® CA (Cocamide DEA) manufactured by Croda, Inc; and a mixture of 1:1 Neodol 45-13:INCROMIDE® CA (Neodol 45-13 being a $C_{14}$–$C_{15}$ linear primary alcohol ethoxylate) manufactured by the Shell Chemical Company.

Other optional ingredients in the compositions of the present invention include inert, water-soluble fillers such as sodium sulphate, which are used to bulk up the extruded formulation. The filler may be a single salt or mixture of salts, which is preferably neutral, or only mildly acidic or alkaline, e.g., alkali metal carbonates, bicarbonates, sulphates, citrates and phosphates.

The compositions of the present invention are particularly suitable for use in fabricating toilet block elements, such as toilet rim blocks for use under the rim of a toilet bowl, and free-standing or "in-cistern" blocks for emersion in a toilet cistern. Toilet block elements of this type, containing the compositions of the present invention, function to release active agent in a controlled manner upon contact with water and are, thus, adapted to release a determined amount of active agent into a toilet bowl each time the toilet flushes.

A toilet rim block according to the present invention may be provided with an appropriate dispensing structure, for example, a cage, or suspension means for mounting the toilet rim block on the rim of a toilet bowl. The toilet blocks of the present invention may also be contained in a temporary water-soluble wrapping, for example, a water-soluble polymeric sheet, which is dissolved away by the water in the toilet bowl or cistern. In particular, toilet blocks of the present invention may be stored between heat sealed sheets to provide control over the release of the components of the block on exposure to water.

The following examples serve to illustrate embodiments of the present invention. It should be understood that these examples are illustrative only.

EXAMPLE A

The following anhydrous, hydrophobic fragrance mixture is produced:

| Ingredients | Parts by Weight |
| --- | --- |
| 5-nonenol-1 | 450 |
| 5-octenol-1 | 450 |
| cis-3-hexenyl ester of cyclopropyl carboxylic acid | 8 |
| bergamot oil, anhydrous | 150 |
| orange oil, anhydrous | 200 |
| lemon oil, anhydrous | 50 |
| ylang oil, anhydrous | 2 |
| γ-methyl ionone | 20 |
| Vetiver Venezuela (anhydrous) | 18 |
| ethyl 4-(3'-methyl butyl) cyclohexyl ether (anhydrous) | 18 |
| 1,5,9-trimethyl cyclododecatriene-1,5,9 | 12 |

The resultant perfume formulation (APRIL® 742) is a "woody cologne" formulation.

EXAMPLE B

The following anhydrous, hydrophobic fragrance mixture is produced:

| Ingredients | Parts by Weight |
| --- | --- |
| 5-nonenol-1 | 450 |
| 5-octenol-1 | 450 |
| cis-3-hexenyl ester of cyclopropyl carboxylic acid | 8 |
| bergamot oil, anhydrous | 150 |
| orange oil, anhydrous | 200 |
| lemon oil, anhydrous | 50 |
| ylang oil, anhydrous | 2 |
| γ-methyl ionone | 20 |
| Vetiver Venezuela (anhydrous) | 18 |
| ethyl 4-(3'-methyl butyl) cyclohexyl ether (anhydrous) | 18 |
| 2-acetyl-1,5,9-trimethyl cyclododecadiene-5,9 | 12 |

The resultant perfume formulation (APRIL® 982) is a "woody cologne" formulation.

EXAMPLE 1

The following formulations were prepared at ambient temperature and pressure and the 50 gram blocks were tested for foam behavior, odor strength/appreciation and weight loss over the life-time of the block:

| Ingredient | A (% w/w) | B (% w/w) | C % w/w |
| --- | --- | --- | --- |
| MARLON® ARL | 50 | 50 | 50 |
| 80:20 polymer:fragrance (powdered) | — | — | 25 |
| polyvinyl alcohol [85% hydrolyzed polyvinyl acetate] (powdered) | — | 20 | — |
| fragrance April® 742 (as described in Example A) | 5 | 5 | — |
| sodium sulphate | 45 | 25 | 25 |

Sample D, having the following ingredients, was also prepared, on the basis of the technology in U.S. Pat. No. 5,543,439, and the 15 gram block tested for foam behavior, odor, strength/appreciation and weight loss over the life-time of the block:

| | |
|---|---|
| MOWIOL® 10-74 | 60% w/w (74% hydrolyzed polyvinyl acetate); |
| UFARYL® DL 90C | 10% w/w (sodium dodecylbenzene sulfonate, 90% a.m.); |
| TEXAPON® K12 | 5% w/w (sodium lauryl sulphate 85% a.m.); |
| POLYOX® 303 | 5% w/w (high molecular weight polyethylene glycol); and |
| APRIL® 742 | 20% w/w (described in Example A, supra). |

MOWIOL® 10-74 is a 74% hydrolyzed polyvinyl alcohol manufactured by American Hoeschst Corporation of Parsippany, N.J., molecular weight 15,000–27,000, melting point 190° C., viscosity range 8.5 to 11.5 centipoises; and The polymer:fragrance blend used in formulation C contained 20% w/w of fragrance APRIL® 742 (described in Example A, supra) and 80% w/w MOWIOL® 10-74 polyvinyl alcohol.

The results of the odor and foam evaluations are set out below:

| | Odor Performance | | | |
|---|---|---|---|---|
| Flushes | A | B | C | D |
| 10× | 3.4 | 2.8 | 3.4 | 2.0 |
| 50× | 3.2 | 3.5 | 4.2 | 3.7 |
| 150× | 3.8 | 3.8 | 4.0 | 4.2 |
| 250× | — | 2.7 | 3.2 | 4.0 |

Note: Evaluations carried out using an accelerated test cycle.

Formulation C showed the best overall performance on odor (better than formulation D up until 150 flushes, and then slightly worse than formulation D after 250 flushes).

| | Foam Behavior | | | |
|---|---|---|---|---|
| Flushes | A | B | C | D |
| 34× | D1 | C2 | C2 | 0 |
| 51× | D3 | D3 | D2 | A− 0.5 |
| 102× | D5 | D5 | D2 | B2.5 |
| 153× | C+ 2 | D7 | D4 | B3 |
| 221× | — | D4 | D4 | B2 |
| 255× | — | D5 | D5 | C1.5 |
| 340× | — | D5 | D5 | B+ 2 |

The above results used the following scale (by S. C. Johnson):

A letter is used to describe the foam coverage given by the toilet blocks as follows:

0=less than 25% foam coverage;
A=25% foam coverage;
B=50% foam coverage;
C=75% foam coverage; and
D=100% foam coverage.

A number is then placed after the letter, this number indicating the duration of the foam after the initial flush, as follows:

0=foam duration was nonexistent;
1=one minute;
2=two minutes;
3=three minutes;
4=four minutes;
5 =greater than five minutes; and
10=greater than 10 minutes.

Compared to formulation A, formulation B (polyvinyl alcohol and fragrance separately mixed) showed good foaming during the total lifetime of the block. Slightly worse, but still very good was the foaming performance of formulation C (polymer:fragrance blend).

Weight Loss

The results of the weight loss analysis are shown in FIG. 1.

The expected life time of formulation D is 375 flushes and both formulations B and C are expected to last for 425 flushes. Formulation A was used up after about 225 flushes. Blocks B and C showed no drooling.

Thus, it can be seen from this set of results that toilet blocks containing powdered polyvinyl alcohol (formulations B and C) showed good performance on odor, foaming and life-time. Formulation C (80:20 powdered polymer:fragrance blend) showed a slightly better result in the odor evaluation tests than formulation B, whilst the foaming behavior of formulation B (polyvinyl alcohol and fragrance separately mixed) appeared to be slightly better than formulation C.

EXAMPLE 2

The following series of toilet blocks were tested, in-use, for foam behavior, odor strength/appreciation and weight loss over the lifetime of the block:

| Ingredient | A1 | B1 | C1 | D1 |
|---|---|---|---|---|
| "LABS" | + | + | + | + |
| Polyvinyl alcohol [85% hydrolyzed polyvinyl acetate] | − | + | − | + |
| Fragrance (Example A) | + | + | − | + |
| "LABS":polyvinyl alcohol [85% hydrolyzed polyvinyl acetate]:fragrance blend powdered) | − | − | + | − |
| SLS (powdered cellulose) | − | − | − | + |
| Salt (NaCl) | + | + | + | − |

Blocks A1, B1 and C1 weighed 50 grams and block D1 weighed 15 grams.

Formulation D1 was prepared on the basis of the technology in U.S. Pat. No. 5,543,439. The "LABS":polyvinyl alcohol:fragrance blend of formulation C1 was also prepared on the basis of the technology in U.S. Pat. No. 5,543,439, but the blend was then subsequently ground to form a powder, and then mixed with the other ingredients of formulation C1.

The polyvinyl alcohol used in formulation B1 was also powdered.

The fragrance used in each of these formulations was APRIL® 742 (as described in Example A, supra). The tests were then repeated using corresponding formulations A2, B2, C2 and D2, which are the same as formulations A1, B1, C1 and D1, except that they contain a different fragrance, APRIL® 982 (described in Example B supra). The results of the tests conducted using formulations A1, B1, C1 and D1, and A2, B2, C2 and D2, are set out below:

| Person | Odor Performance | | | | | | | | | | | | | | | | | | | | | | |
|---|---|---|---|---|---|---|---|---|---|---|---|---|---|---|---|---|---|---|---|---|---|---|---|
| | 27 Flushes | | | | | 60 Flushes | | | | | 160 Flushes | | | | | 250 Flushes | | | | | 330 Flushes | | | |
| Code | 1 | 2 | 3 | 4 | 5 | 1 | 2 | 3 | 4 | 5 | 1 | 2 | 3 | 4 | 5 | 1 | 2 | 3 | 4 | 5 | 1 | 2 | 4 | 5 |
| A1 | 2.5 | 1.0 | 2.7 | 3.0 | 3.3 | 2.0 | 3.0 | 1.8 | 3.7 | 1.0 | 4.0 | 2.7 | 3.3 | 2.7 | 2.7 | 2.0 | 3.0 | 2.7 | 3.0 | 3.0 | | | | |
| B1 | 2.0 | 3.0 | 3.0 | 2.7 | 3.3 | 3.5 | 3.7 | 2.8 | 2.8 | 2.0 | 3.5 | 3.0 | 4.0 | 3.0 | 3.0 | 3.5 | 4.0 | 4.3 | 4.0 | 3.8 | 2.0 | 3.0 | 3.0 | 3.3 |
| C1 | 2.5 | 2.7 | 3.5 | 2.7 | 3.1 | 3.0 | 2.8 | 3.5 | 3.3 | 2.0 | 2.5 | 2.7 | 3.5 | 2.0 | 2.8 | 3.0 | 4.7 | 4.3 | 4.0 | 3.3 | 2.5 | 2.5 | 2.8 | 3.0 |
| D1 | 3.5 | 3.0 | 3.5 | 3.3 | 3.6 | 4.5 | 3.0 | 4.0 | 3.7 | 3.0 | 4.0 | 2.7 | 3.5 | 2.7 | 3.3 | 3.5 | 4.0 | 4.0 | 3.7 | 3.5 | 3.0 | 4.0 | 2.8 | 3.8 |
| A2 | 3.0 | 2.7 | 3.0 | 3.8 | 3.8 | 4.0 | 4.0 | 4.3 | 4.0 | 4.0 | 4.0 | 4.3 | 4.5 | 4.0 | 4.0 | 2.0 | 3.7 | 3.0 | 3.5 | 3.0 | | | | |
| B2 | 2.0 | 4.0 | 2.8 | 3.3 | 3.7 | 3.7 | 3.0 | 4.0 | 3.7 | 3.8 | 3.0 | 3.7 | 4.0 | 3.8 | 3.8 | 3.5 | 4.0 | 4.3 | 4.0 | 3.5 | 3.5 | 3.5 | 3.3 | 2.0 |
| C2 | 3.5 | 2.0 | 3.0 | 3.8 | 3.7 | 3.0 | 2.0 | 4.0 | 3.3 | 4.3 | 2.5 | 4.3 | 3.8 | 3.0 | 4.3 | 3.2 | 4.7 | 4.3 | 4.3 | 4.3 | 2.8 | 3.5 | 3.3 | 2.0 |
| D2 | 4.3 | 3.0 | 3.5 | 4.3 | 4.0 | 4.0 | 4.0 | 4.8 | 4.0 | 4.0 | 3.8 | 3.7 | 4.3 | 3.5 | 4.0 | 4.0 | 4.7 | 4.7 | 4.0 | 4.1 | 3.5 | 3.7 | 3.8 | 3.0 |

Numbers 1, 2, 3 are individuals from Personnel Group I (Analytical labs)
Numbers 4, 5 are individuals from Personnel Group II (Odor Evaluation labs)

As the results show, odor performance is fragrance dependent.

In the case of APRIL® 742, formulations B1 and C1 showed comparable results and performed much better than formulation A1 (conventional toilet block), whilst formulation A2 (conventional toilet block) performed slightly better than both formulations B2 and C2 with fragrance APRIL® 982.

In both cases, formulations D1 and D2 had the best odor performance.

It should be noted that toilet blocks A1 and A2 were completely dissolved after about 250 flushes.

| Foam Behavior | | | | |
|---|---|---|---|---|
| No. of Flushes | A1 | B1 | C1 | D1 |
| 150× | D5 | C+ 3 | C4 | B2 |
| 250× | B2 | C+ 5 | D5 | B3 |
| 330× | | C3 | C4 | B2 |
| No. of Flushes | A2 | B2 | C2 | D2 |
| 150× | D5 | C3 | D– 4 | B2 |
| 250× | D– 2 | D4 | D5 | B2 |
| 330× | | C+ 3 | C+ 3 | A1 |

The same scale (by S. C. Johnson) was used as for Example 1.

Compared to formulations A1 and A2 (conventional toilet blocks), the foam behavior of formulations B1 and B2 and C1 and C2, was moderate to good. Formulations C1 and C2 ("LABS":polyvinyl alcohol:fragrance blend) performed slightly better than formulations B1 and B2 ("LABS", polyvinyl alcohol and fragrance separately mixed). Formulations D1 and D2 gave poor and instable foam.

The fragrance type had no effect on foam behavior.

It should be noted that toilet rim blocks A1 and A2 were completely dissolved after about 250 flushes.

Weight Loss

The results of the weight loss analysis are set out in FIGS. 2 and 3.

Compared to formulations B1 and B2, C1 and C2, and D1 and D2, the lifetime of formulations A1 and A2 (conventional toilet blocks) was short (approximately 250 flushes).

Formulations D1 and D2 initially increased in weight (as a result of water absorption), followed by a quick loss in weight (expected lifetime: 350–375 flushes).

Formulations C1 and C2 also increased slightly in weight and then slowly lost weight (expected lifetime: 400–425 flushes).

Only the weight loss of formulations B1 and B2 was found to be dependent on the fragrance used. APRIL® 742 showed the same profile for both formulations B1 and C1, while in the case of APRIL® 982, formulation B2 absorbed more water and the rate of weight loss was much slower than for formulation C2.

In order to determine whether this effect of the fragrances on weight loss of formulations B1 and B2, and C1 and C2, are related to the solubility of the fragrances in water, a so called MIPS test was carried out.

The principle of the MIPS test is as follows. A saturated solution of surfactant is made, then on adding a perfume, the solution becomes overloaded and cloudy. Addition of more water is required to return it to a clear solution. The amount of water that needs to be added to make the solution clear again will vary with different types of perfume. For example, a very insoluble perfume will require much more water to make the solution clear than a soluble perfume.

The results of the MIPS test carried out in respect of the two fragrances used in Example 2 are as follows:

Reduction of solubility of fragrance APRIL® 742 (Example A): 63%; and

Reduction of solubility of fragrance APRIL® 982 (Example B): 62%.

Thus, the differences in solubility between the fragrances used in Example 2 is minimal and it can, therefore, be concluded that the differences in the weight loss of formulations B1 and B2, and C1 and C2, are not related to the solubility of the fragrances.

By comparing the results of the tests carried out in Example 1, with the results of the tests using fragrance APRIL® 742 in Example 2, it can be seen that, in both cases, the foam behavior of formulations B and B1, and C and C1, was found to be (moderate to) good. In Example 1, formulation B performs slightly better than formulation C, whereas in Example 2, formulation C1 performs slightly better than formulation B1.

With regard to odor performance, formulation C showed the best overall performance in Example 1, whereas formulation D1 showed the best overall performance in Example 2, with both formulations B1 and C1 in Example 2 having a better overall performance than formulation A1 (conventional toilet block).

Finally, with regard to weight loss, although the absolute figures were not exactly the same, the trend was comparable.

Thus, in the case of polar fragrances, it can be seen from the above examples that adding neat polymer powder to a conventional toilet block formulation improves fragrance performance and block longevity. Also, the use of polymer powder improves the foaming performance of the U.S. Pat. No. 5,543,439 formulations, without compromising excellent aroma behavior, life-time performance and desired solubility/dispersibility characteristics.

The features disclosed in the foregoing description, in the following claims and/or in the accompanying drawings may both separately and in any combination thereof, be material for realizing the invention in diverse forms thereof.

What is claimed is:

1. A process for forming a toilet block for use in a toilet bowl consisting essentially of the sequential steps of:
   (i) extruding polyvinyl alcohol or 50–90% partially hydrolyzed polyvinyl acetate having a number average molecular weight of from about 15,000 up to about 68,000 and containing 0–15% by weight polar plasticizer to form an extrudate which is water-soluble at a temperature in the range of 25–35° C.;
   (ii) chilling and pelletizing the resulting extrudate at a temperature in the range of from about 5° C. up about 60° C.;
   (iii) cryogenically grinding the resultant pelletized product at a pressure in the range of from about 1 atmosphere up to about 50 atmospheres to a particle size in the range of from about 10 up to about 500 microns to form cryogenically-ground particles;
   (iv) subsequently comminuting the resulting cryogenically-ground particles in order to form a powder;
   (v) mixing the resulting powder with:
      (a) from 1 up to about 20% by weight of a compatible fragrance comprising a major proportion of at least one highly polar organic primary alcohol;
      (b) at least one compatible sulfonate or sulfate-containing surfactant having both detergent and foaming properties; and
      (c) from 25 to 45% by weight of a water-soluble filler selected from the group consisting of alkali metal bicarbonates, alkali metal sulfates, alkali metal carbonates, alkali metal citrates, alkali metal phosphates and sodium chloride; and then
   (vi) molding the resultant mixture into a toilet block.

2. A process for forming a toilet block for use in a toilet bowl consisting essentially of the sequential steps of:
   (i) extruding polyvinyl alcohol or 50–90% partially hydrolyzed polyvinyl acetate having a number average molecular weight of from about 15,000 up to about 68,000 and containing 0–15% by weight polar plasticizer with from 1 up to about 20% by weight of a compatible fragrance comprising a major proportion of at least one highly polar organic primary alcohol for form an extrudate which is water-soluble at a temperature in the range of 25–35° C.;
   (ii) chilling and pelletizing the resulting extrudate at a temperature in the range of from about 5° C. up about 60° C.;
   (iii) cryogenically grinding the resultant pelletized product at a pressure in the range of from about 1 atmosphere up to about 50 atmospheres to a particle size in the range of from about 10 up to about 500 microns to form cryogenically-ground particles;
   (iv) subsequently comminuting the resulting cryogenically-ground particles in order to form a powder;
   (v) mixing the resulting powder with:
      (a) at least one compatible sulfonate or sulfate-containing surfactant having both detergent and foaming properties; and
      (b) from 25 to 45% by weight of a filler selected from the group consisting of alkali metal bicarbonates, alkali metal sulfates, alkali metal carbonates, alkali metal citrates, alkali metal phosphates and sodium chloride; and then
   (vi) molding the resultant mixture into a toilet block.

3. The toilet block produced according to claim 1.

4. The toilet block produced according to claim 2.

* * * * *